United States Patent [19]
Lambert

[11] Patent Number: 5,482,031
[45] Date of Patent: Jan. 9, 1996

[54] ARRANGEMENT FOR CONNECTING A PATIENT TO A RESPIRATOR, AND THE USE OF A MOISTURE-HEAT-EXCHANGER IN THE ARRANGEMENT

[75] Inventor: Hans Lambert, Stockholm, Sweden

[73] Assignee: Gibeck Respiration AB, Väsby, Sweden

[21] Appl. No.: 192,980

[22] Filed: Feb. 8, 1994

Related U.S. Application Data

[63] Continuation of Ser. No. 946,925, Sep. 17, 1992, abandoned.

[30] Foreign Application Priority Data

Sep. 20, 1991 [SE] Sweden ................................ 9102731

[51] Int. Cl.[6] .................................................. A61M 15/00
[52] U.S. Cl. ................. 128/203.12; 128/203.26; 128/204.16; 128/204.17
[58] Field of Search .................. 128/203.12, 203.16, 128/203.17, 203.26, 203.27, 204.17, 205.13, 207.14, 204.16

[56] References Cited

U.S. PATENT DOCUMENTS

| 404,986 | 6/1889 | Rudolfy | 128/204.17 |
|---|---|---|---|
| 603,021 | 4/1898 | Dight | 128/201.13 |
| 1,808,177 | 6/1931 | Pütter | 128/204.17 |
| 3,190,287 | 6/1965 | Miller, Jr. | 128/205.24 |
| 3,912,795 | 10/1975 | Jackson | 128/207.14 |
| 4,224,939 | 9/1980 | Lang | 128/207.14 |
| 4,248,217 | 2/1981 | Brisson | 128/204.17 |
| 4,589,409 | 5/1986 | Chatburn et al. | 128/203.26 |
| 4,727,871 | 3/1988 | Smargiassi et al. | 128/204.17 |
| 5,080,093 | 1/1992 | Raabe et al. | 128/204.17 |

FOREIGN PATENT DOCUMENTS 167364  6/1959  Sweden .

Primary Examiner—Aaron J. Lewis
Attorney, Agent, or Firm—Oblon, Spivak, McClelland, Maier, & Neustadt

[57] ABSTRACT

An arrangement for connecting a patient to a respirator (1) comprising a humidifier (8) for humidifying gas inspired by the patient. The arrangement also comprises a moisture-heat-exchanger (10) whose one side is connected to the respirator inlet and outlet (2,3) and whose other side is connected to the patient such that inspired gases pass the humidifier (8) before reaching the patient and expired gases do not pass the humidifier.

4 Claims, 1 Drawing Sheet

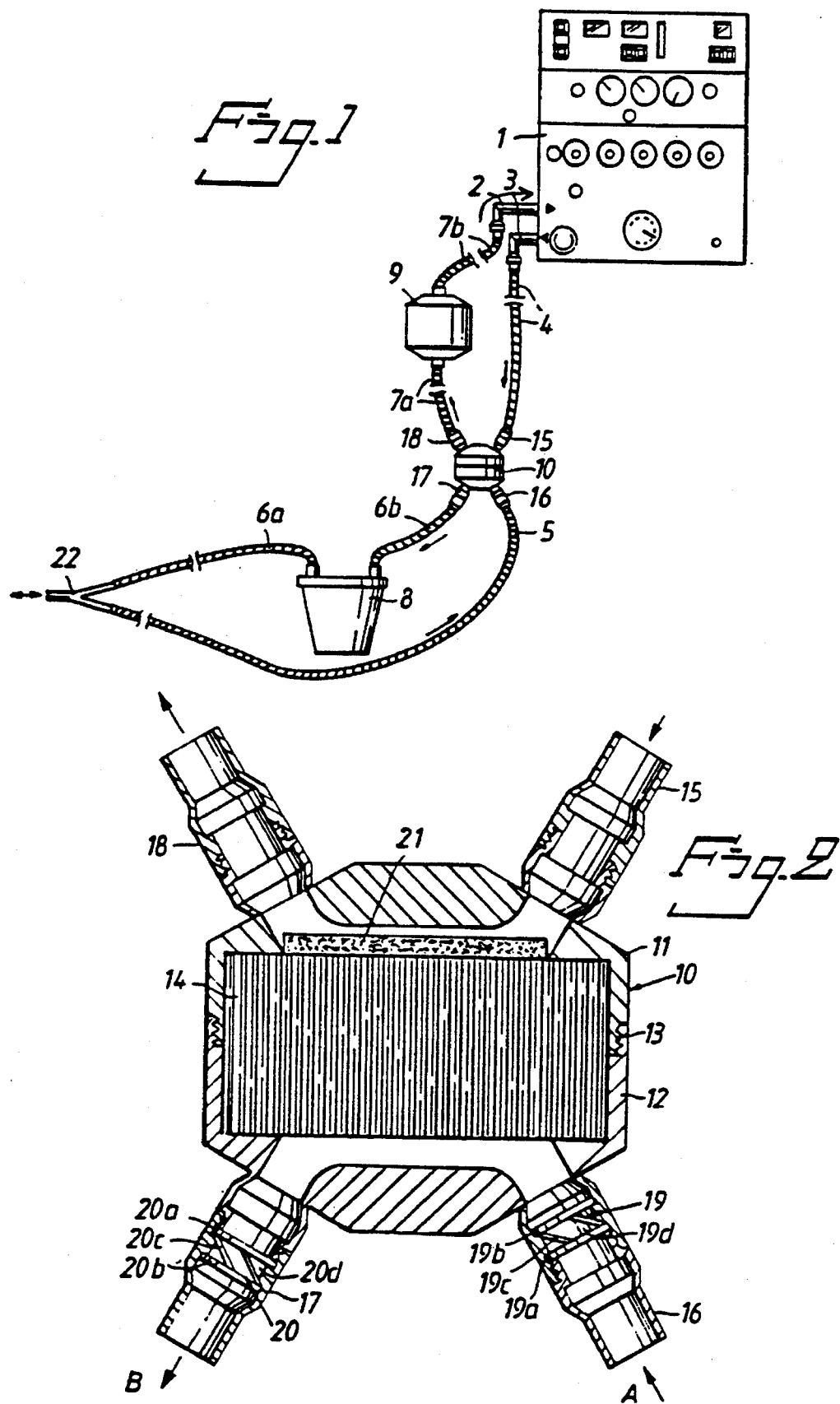

2

ARRANGEMENT FOR CONNECTING A PATIENT TO A RESPIRATOR, AND THE USE OF A MOISTURE-HEAT-EXCHANGER IN THE ARRANGEMENT

This application is a continuation, of application Ser. No. 07/946,925 filed Sep. 17, 1992, now abandoned.

DESCRIPTION

1. Technical Field

The present invention relates to an arrangement for connecting a patient to a respirator which is provided with inlet and outlet for gas expired and inspired by the patient, and also to the use of a moisture-heat-exchanger in said arrangement.

2. Background Art

A patient connected to a respirator inspires moist air which, via a humidifier, is fed out from the respirator, and expires moist air, which is introduced into the respirator. Due to the humidifier, the expired air has a considerable moisture content and condenses within the respirator and therewith contaminates the respirator, therewith necessitating, among other things, cleansing and sterilization of the respirator at regular intervals. When using more modern types of respirator which include sensitive sensors, the moist air is also liable to have a negative influence on these components and is liable to result in damage to those which come into contact with condensation, or during the sterilization process.

In order to solve the aforesaid problems, a filter has been coupled between the patient and the respirator inlet, in which bacteria and moisture collect, this moisture condensing in the filter container. When the container has been filled with a given volume of condensed water, the resistance to flow through the filter container becomes so great as to necessitate removal of the filter container, which is then discarded and replaced with a new container and filter. If this procedure is not followed, the safety of the patient is jeopardized. It is often necessary to change the filter and container three to four times each day, which is both time-consuming and expensive, since containers and filters of this kind demand a relatively high price.

DISCLOSURE OF THE INVENTION

An object of the present invention is to avoid the drawbacks associated with the aforedescribed arrangements and to provide an arrangement which obviates the use of the aforesaid filter or with which it is only necessary to replace the filter after long periods of use.

This object is fulfilled with an inventive arrangement having the features set forth in the characterizing clauses of respective claims.

BRIEF DESCRIPTION OF THE DRAWING

FIG. 1 is a schematic view of the inventive arrangement and shows the arrangement coupled between a patient and a respirator; and FIG. 2 is a sectional view through the arrangement illustrated in FIG. 1.

PREFERRED EMBODIMENT

FIG. 1 illustrates a conventional respirator 1 which is provided with an inlet 2 and an outlet 3. The respirator 1 is connected to a patient (not shown) by means of hoses 4, 5, 6a, 6b, 7a and 7b, and an active air humidifier 8, a bacteria filter 9, the inventive arrangement, referenced 10, and a Y-piece 22.

The respirator outlet 3 for expiration gases is connected, by means of the hose 4, to the arrangement 10 which is connected to the Y-piece 22 via the hose 6b, the active air humidifier 8 and the hose 6a. The Y-piece 22 is connected to the patient in a conventional manner. The Y-piece 11 is connected to the arrangement 10 through the intermediary of the hose 5, and the arrangement 10 is connected to the respirator inlet 2 through the intermediary of the hose 7a, the bacteria filter 9 and the hose 7b.

Thus, the gases that are inspired by the patient pass through the arrangement 10 and the air humidifier 8, whereas the gas expired by the patient passes through the arrangement 10 and the bacteria filter 9.

The air humidifier 8 is a conventional, active air humidifier which contains an electrically heated water bath through which the gas is forced to pass before being administered to the patient. The bacteria filter 9 is also of a conventional kind and is comprised of a container with a filter constructed from siliconized glass fibre. The bacteria filter 9 is not essential to the function of the inventive arrangement and can therefore be omitted.

As shown more clearly in FIG. 2, the arrangement 10 includes a casing or housing which is comprised of two parts 11 and 12 and which has a substantially circular-cylindrical shape with ends in the form of truncated cones. The parts 11 and 12 are detachably screwed together on each side at 13. Removably placed in a circular-cylindrical cavity in the housing 11, 12 is a moisture-heat-exchanger element 14 which is of the kind used in conventional moisture-heat-exchangers and which may also be comprised of one or more corrugated bands of heat-and-moisture absorbing and heat-and-moisture emitting paper material which is wound to cylinder form. Those channels in the element 14 through which gas and moisture pass and which are formed between the band layers extend parallel with the centre axis of the cylinder. The element 14 substantially fills the whole of the cavity in the housing 11, 12. The element 14 may also be constructed so as to filter the gases, or may be supplemented with a filter part 21, which is mounted in the housing 11, 12 on the upper side (the illustrated side) of the element and/or on its underside. The arrangement 10 is made as small as possible, in order to minimize the amount of expiration gas collected, this gas containing carbon dioxide and liable to be returned to the patient in the inspiration phase of a breathing cycle.

The housing parts 11 and 12 are provided with four, preferably identical connectors 15, 16, 17 and 18 to which the hoses 4, 5, 6b and 7a are detachably connected. The connector 15 is connected to the hose 4, the connector 16 to the hose 5, the connector 17 to the hose 6b and the connector 18 to the hose 7a, as illustrated in FIG. 1. Each connector 15–18 is comprised of an inner part which is firmly fixed to the housing 11, 12 and an outer part which is screwed firmly onto the inner part. Check valves 19 and 20 are mounted in respective connectors 16 and 17. Each check valve 19, 20 is comprised of a one-piece plastic element comprising a sleeve 19d and 20d respectively with a respective ring-shaped seat 19a and 20a, which are firmly clamped between the two connector parts, and a cap 19b and 20b respectively which is firmly connected to and normally seals (as shown) against the sleeve, through the intermediary of a plurality of respective spring legs 19c and 20c surrounding the sleeve. In the connector 16, the cap 19b is located above the seat 19a, whereas in the connector 17 the cap 20b is located beneath the seat 20a, meaning that gas is allowed to pass through the connector 16 in the direction of the arrow A towards the arrangement 10 and that gas is permitted to pass through the connector 17 in the direction of the arrow B, by removing respective caps 19b and 20b from respective sleeves 19d and 20d. Respective caps 19b and 20b are pressed against respective sleeves 19d and 20d, so as to prevent gas from passing in the opposite directions. The connectors 15–18 communicate with the cavity in which the element 14 is inserted, through holes in the walls of the housing 11, 12.

When using the inventive arrangement, as it is connected in FIG. 1, gas is discharged from the respirator outlet 3 during the gas inspiration cycle of the patient and exits through the connector 15 in the arrangement 10. Subsequent to the gas having passed through the element 14, and entraining moisture therefrom, the gas enters the connector 17 and is then delivered to the patient via the open check valve 20 and then through the humidifier 8. In this phase, the check valve 19b prevents gas from entering the connector 16. Since the respirator inlet 2 is blocked within the respirator, no appreciable amount of gas will pass through the connector 18.

During the expiration cycle of the patient, expiration gas is delivered through the connector 16. Subsequent to the gas having passed the same parts of the element 14, which earlier have been passed by the inspiration gas, the dehumidified gas enters the connector 18 and is passed further to the patient, via the bacteria filter 9. The check valve 20 therewith prevents gas from being drawn in through the connector 17 from the humidifier 8 to the filter 14. The outlet 3 is closed within the respirator 1 during the expiration cycle, and consequently no gas is passed out through the connector 15.

The aforedescribed arrangement can be modified without departing from the inventive concept. For example, it is possible to use only one of the aforesaid check valves 19 20, and it is also possible to provide a total of only two connectors on the housing 11, 12 instead of two inlet connectors 15, 16 and two outlet connectors 17, 18, of which connectors one is connected to the hoses 4 and 7a through the intermediary of a T-piece or Y-piece, and the other connector is connected to the hoses 5 and 6b through the intermediary of a T-piece or Y-piece. It is also possible to provide a total of three connectors on the housing 11, 12, with one of the connectors being connected to a T-piece or Y-piece and the remaining two connectors being connected to the hoses 5 and 6b or 4 and 7a. When a T-piece or Y-piece is used, the connector connected to said piece is suitably fitted along the centre axis of the arrangement 10. When using T-pieces or Y-pieces, the check valves can be placed in said pieces instead of the connectors.

The invention is only restricted by the features set forth in the following claims.

I claim:

1. An arrangement for dehumidifying air comprising a respirator having an inlet connected to a patient and an outlet including a moisture-heat-exchanger having one side connected to separate first and second conduits which are connected to said inlet and outlet, respectively, said moisture-heat-exchanger having another side adapted to be connected through separate third and fourth conduits to a patient such that inspired and expired gases are separated from each other between said other side and the patient, at least one of said third and fourth conduits containing a check valve connected to said moisture-heat-exchanger whereby gases are free to flow from the exchanger to the patient through the third conduit and to the exchanger from the patient through the fourth conduit, said moisture-heat-exchanger absorbing moisture from the expired gases before reaching the respirator inlet, and moisture from the moisture-heat-exchanger being at least partly emitted by means of the gases from the respirator outlet to the patient, and a humidifer located in the third conduit whereby the gases inspired by the patient will be humidified by the humidifier after having passed the moisture heat-exchanger.

2. An arrangement as set forth in claim 1 in which both the third and fourth conduits contain check valves.

3. An arrangement according to claim 2, wherein a filter, such as a bacteria filter, is located in the first conduit between the respirator inlet and the moisture-heat-exchanger.

4. An arrangement according to claim 2, wherein the moisture-heat-exchanger includes a filter part.

* * * * *